United States Patent [19]

Brooker et al.

[11] 4,026,290

[45] May 31, 1977

[54] METHOD OF ADMINISTERING MEDICAMENTS THROUGH THE SKIN

[75] Inventors: Peter John Brooker; John Goose, both of Saffron Walden, England

[73] Assignee: Fisons Limited, England

[22] Filed: Nov. 18, 1975

[21] Appl. No.: 633,081

[30] Foreign Application Priority Data

Nov. 30, 1974 United Kingdom ............ 51941/74

[52] U.S. Cl. .............................. 128/260; 128/268
[51] Int. Cl.² .......................................... A61F 7/02
[58] Field of Search ............................ 128/260, 268

[56] References Cited
UNITED STATES PATENTS

| | | | |
|---|---|---|---|
| 2,676,593 | 4/1954 | Cheneweth | 128/268 |
| 3,598,123 | 8/1971 | Zaffaroni | 128/268 |
| 3,788,296 | 1/1974 | Klatt et al. | 128/268 |
| 3,814,097 | 6/1974 | Ganderton et al. | 128/268 |
| 3,896,789 | 7/1975 | Trancik | 128/268 |

*Primary Examiner*—Louis G. Mancene
*Assistant Examiner*—Robert F. Cutting
*Attorney, Agent, or Firm*—Wenderoth, Lind & Ponack

[57] ABSTRACT

There are provided means for the extended application of a systemic medicament to the skin of an animal, especially for prophylaxis, which means comprises in combination, a systemic medicament composition containing a carrier which is capable of transmitting the medicament through the skin, and attachment means for contacting the medicament composition with a portion of the skin of the animal.

4 Claims, 7 Drawing Figures

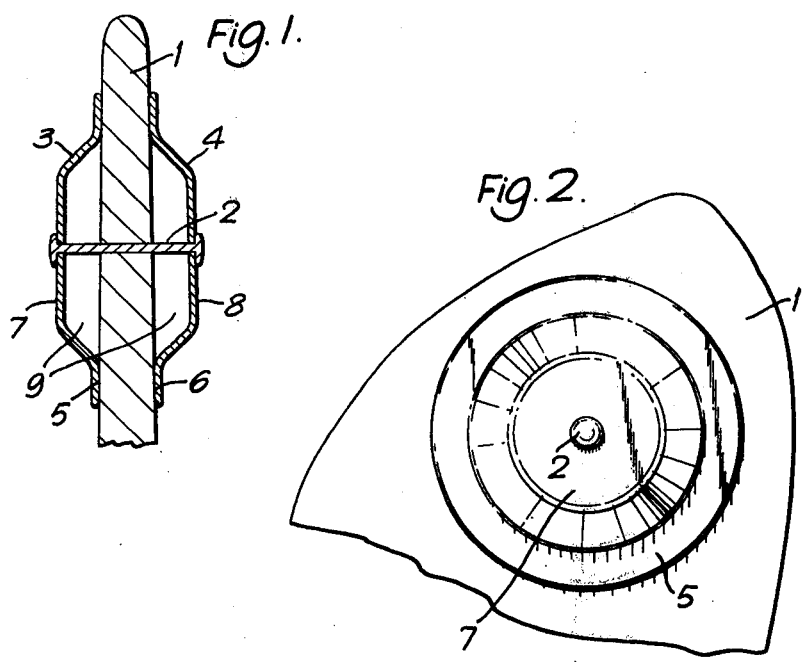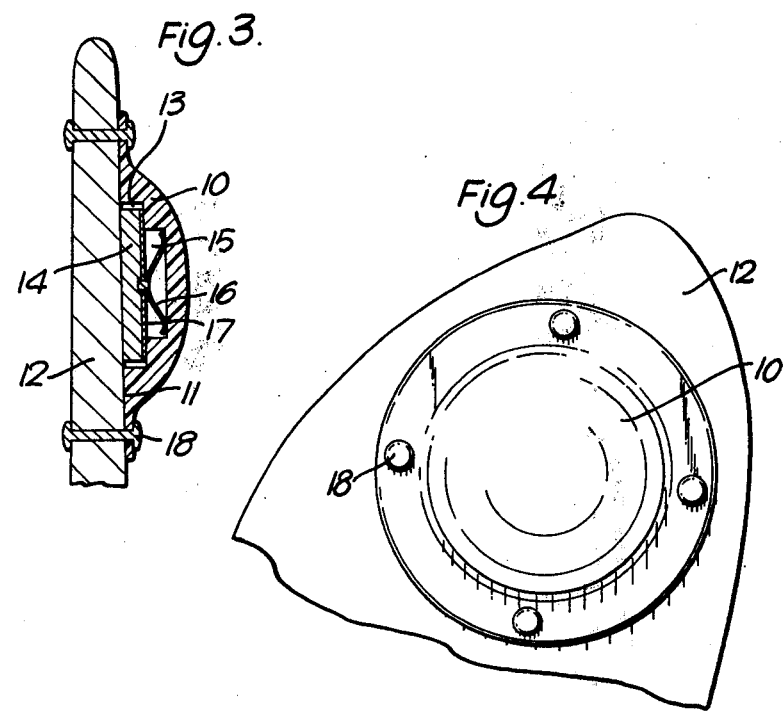

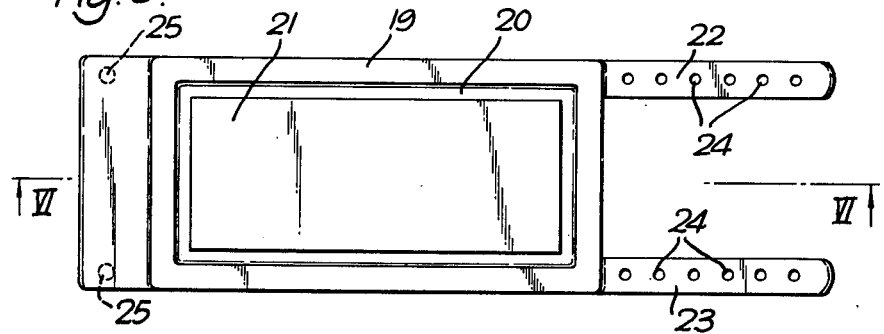
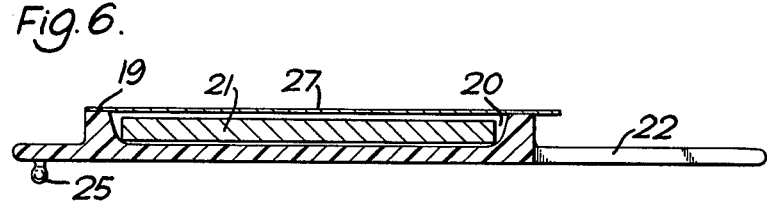
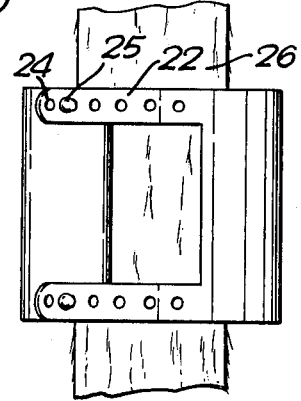

METHOD OF ADMINISTERING MEDICAMENTS THROUGH THE SKIN

This invention concerns devices for the extended application of a medicament of the skin of the animal.

Many medicaments are known are prophylactic, that is to say which are active to prevent the occurrence of disease or disorder as compared with those which are active against a disease or disorder only when it occurs. However, prophylactic medicaments to be effective need normally to be administered in low doses and very often, and such a procedure is necessarily time-consuming and inconvenient.

We have now discovered a means whereby medicaments may be continuously and conveniently administered to an animal (including humans) over an extended period of time.

Accordingly, in one aspect, this invention provides a means for the extended application of a systemic medicament to the skin of an animal, which means comprises, in combination, a systemic medicament composition containing a carrier which is capable of transmitting the medicament through the skin, and attachment means for contacting the medicament composition with a portion of the skin of the animal.

To ensure that the application of the medicament is 'extended', by which term is meant periods of hours, days, weeks or months rather than periods of seconds or minutes, the attachment means must be such that, under normal conditions, the device will not be removable by the animal for example by licking or scratching.

The attachment means for contacting the medicament with a portion of the skin of the animal may be any attachment means which is appropriate having regard to the form of the particular medicament composition. For example, when a solid composition is employed, the attachment means may be simply a strap which extends around a portion of the animal's body, for example around a limb or the tail, the medicament composition being located between the strap and the animal's skin and being retained in position by the strap.

However, the preferred attachment means, which may be employed with liquid or semi-solid compositions in addition to solid compositions, are those which comprise a device having a basal surface area adapted to contact the skin of the animal, in which area are provided one or more depressions adapted to contain the medicament, and means for attachment of the device to the animal such that the basal surface area contacts the skin of the animal.

The device may be attached to the skin of the animal if desired by means of an adhesive, for example by an adhesive located on the basal surface area thereof. However, although this method of attachment is perfectly satisfactory where the human skin is involved (the device then possibly being in the form of a conventional sticking plaster), for ease of application to the hair covered skin of an animal and to lessen the likelihood of removal accidentally, mechanical means are preferred, for example one or more clips or, where appropriate, pins or staples.

The medicament compositions may be attached wherever desired to the skin of the animal, but for convenience of attachment to, and to lessen the likelihood of removal from, the skin of an non-human animal, attachment to the ears or tail by means of a device as described hereinbefore is preferred. For attachment to the ears, the device may be pinned, clipped or stapled onto the ears in any convenient manner, and for attachment to the tail the device may extend circumferentially around the tail and be clamped on the tail by appropriately securing together for example by clips the free ends of the device. It will be appreciated that there are many ways of attaching the device to the animal.

When attached to the animal, the basal surface area of the device must naturally make such contact with the skin of the animal as to prevent the medicament escaping from the depression(s) in which it is contained except by absorption into the animal through that portion of its skin in contact therewith. This naturally depends upon the formulation of the medicament, which may conveniently be in a form which does not flow well, since this allows some imperfection in the sealing of the basal surface area to the skin without loss of medicament. Imperfection in sealing also allows air to circulate between the device and the animal's skin and avoids the disadvantages normally associated with occlusion.

The devices may be constructed, for example, of a metal, such as aluminium, or a plastics material, such as nylon.

Most desirably, the material of which the device, or at least the basal surface area thereof, is constructed, is flexibly resilient such that the device may conform to some extent to the skin of the animal to which it is applied, especially in the case of a device for application to the tail of an animal.

Depending on the nature of the formulation of the medicament, the device may be applied directly onto the hair or parted fleece of the animal or the area of skin to which the device is to be applied may be shaved and cleansed before the device is applied.

The method of the present invention is of particular use in applying medicaments such as travel sickness mitigators, anti-migraine compounds or analgesics to humans and in applying medicaments such as anthelmintics, antiprotozoal agents, insecticides, miticies and acaricides to domestic or farm animals, such as sheep, pigs, cattle, horses, goats, dogs and cats. When appropriately formulated, we have found that certain compounds may be absorbed through the skin of such animals to give a prophylactic effect.

Examples of compounds which may be so formulated are:

a. motion sickness mitigators, e.g. scopolamine hydrobromide,
b. anti-migraine compounds, e.g. ergotamine tartrate,
c. analgesics, e.g. paracetamol, 4-hydroxyacetanilide,
d. anthelmintics, e.g. Tetramisole (2,3,5,6-tetrahydro-6-phenylimidazo [2,1-b]thiazole especially the laevo isomer, or a salt thereof), Thiabendazole [2-(4-thiazolyl)benzimidazole or a salt thereof], carbon tetrachloride, Parbendazole (methyl 5-butyl-benzimidazole-2-carbamate or salt thereof), Hexachlorophene [2,2'-methylenebis-(3,4,6-trichlorophenol or a salt thereof], Methyridine [2-(2-methoxyethyl)-pyridine or a salt thereof], Nitroxynil (4-hydroxy-3-iodo-5-nitrobenzonitrile or a salt thereof), Rafoxanide [3-chloro-4'-(p-chlorophenoxy)-3,5-diiodosalicylanilide or a salt thereof], Oxyclozanide 3,3',5,5',6-pentachloro-2,2'-dihydroxybenzanilide or a salt thereof), Benomyl (methyl 1-[butylcarbomoyl]benzimadazole-2-carbamate), Bavistin (methyl benzimidazole-2-carbamate or a salt thereof), Thiophanate (diethyl 4,4'-o-phenylenebis[3-thioallophanate]), Oxibendazole (methyl 5-propoxy-benzimidazole-2-carbamate or a salt thereof), triphenylbismuth, triphenylbismuth dinitrate, triphenylbismuth dichloride, and triphenylbismuth difluoride, 4,5,6-trichloro-7-(diethylsulphamoyl)-2-trifluoromethyl)benzimidazole;

4-bromo-5,6-dichloro-7-(diethylsulphamoyl)-2-(trifluoromethyl)benzimidazole;

4,5,6-tribromo-7-(diethylsulphamoyl)-2-(trifluoromethyl)benzimidazole;

4,6-dibromo-5-chloro-7-(diethylsulphamoyl)-2(trifluoromethyl)benzimidazole;

4,5,6-trichloro-7-(ethylsulphamoyl)-2-(trifluoromethyl)benzimidazole;

4,5,6-trichloro-7-(methylsulphamoyl)-2-(trifluoromethyl)benzimidazole;

4,5,6-trichloro-7-(n-propylsulphamoyl)-2-(trifluoromethyl)benzimidazole; and salts of the benzimidazoles; 2,3,5,6-tetrahydro-6-phenyl-imidazo[

1-(Diethylcarbamoyl)-4-methylpiperazine or pharmaceutically acceptable salts thereof;

trans-1,4,5,6-tetrahydro-1-methyl-2-[2-(2-thienyl)-vinyl]pyrimidine or pharmaceutically acceptable salts thereof;

trans-1,4,5,6-tetrahydro-1-methyl-2-[2-(3-methyl-2-thienyl)vinyl]pyrimidine or pharmaceutically acceptable salts thereof;

methyl 5(6)-benzoyl-2-benzimidazolecarbamate; or isopropyl 2-(4-thiazolyl)benzimidazole-5carbamate:

2-Acetoxy-3,4'-dibromo-5-chlorothiobenzanilide; or 3,3'-Dichloro-5,5'-dinitro-o,o'-biphenol;

e. antiprotozoal compounds, e.g.

4,4'-(Pentamethylenedioxy)dibenzamidine and pharmaceutically acceptable salts thereof;

4,4'-(Trimethylenedioxy)dibenzamidine and pharmaceutically acceptable salts thereof;

4,4'-Oxydibenzamidine and pharmaceutically acceptable salts thereof;

3,3'-Diamidinocarbanilide and pharmaceutically acceptable salts thereof; and 3,3'-Di(2-imidazolin-2-yl)carbanilide and pharmaceutically acceptable salts thereof.

f. systemic insecticides, miticides and acaricides, e.g.

Ruelene — 4-t-butyl-2-chlorophenyl methyl N-methylphosphoramidate trichlorphon — dimethyl (2,2,2-trichloro-1-hydroxyethyl)phosphonate fenthion — O,O-dimethyl-O-(4-methylthio-m-tolyl)-phosphorothioate phosmet — O,O-dimethyl-S-(Phthalimidomethyl)-phosphorodithioate amitraz — N,N-di(2,4-xyliminomethyl)methylamine chlordimeform — N'-(4-chloro-o-tolyl)-N,N-dimethylformamidine Solutions are particularly good for transmitting the compounds through the skin, but are generally very highly efficient, transmitting greater quantities through the skin than are required merely for prophylaxis unless a means of metering the solution to the skin is also employed. Such a means may conveniently comprise a solution of the medicament absorbed onto a porous, solid carrier, for example fired clay, a rigid synthetic foam or a fibrous material such as cotton wool, which may, if desired, be blanked off over part of its surface area so as to leave only the remaining surface area thereof in contact with the animal's skin. The compositions may alternatively be in the form of a cream, paste or gel, formulated with conventional adjuvants or carriers to give a suitable consistency and duration of activity (preferably 1 week to 4 months) when the device is attached to an animal. Suitable adjuvants and carriers include, for example, lanolin, gelling agents, polyethylene glycol, wetting agents and surfactants.

The preparation of an appropriate formulation, having regard to a predetermined area of contact thereof with the animal's skin, to give a suitable rate of absorption of medicament over an extended period is believed to be within the competence of those skilled in the preparation of pharmaceutical formulations.

Up to the time of application to the skin of the animal, the formulation is either stored separately and used as required, for example by placing in the depression(s) in a device as hereinbefore described, or, more preferably, is already in the depression(s) in such a device and retained therein by suitable means, for example by a strippable foil or plastic sheet, which is desirably airtight. Such a strippable foil or sheet would, of course, be removed before application of the device to the animal.

In another aspect, this invention provides per se a device, other than a sticking plaster, for the extended application of a medicament to the skin of an animal, which device comprises a basal surface area adapted to contact the skin of an animal, in which area there are provided one or more depressions adapted to contain a medicament, and means for attachment of the device to the animal such that the basal surface area contacts the skin of the animal.

This invention also provides a method of applying a medicament continuously over an extended period of time to the skin of an animal, which method comprises attaching by means as hereinbefore described a medicament composition containing a carrier which is capable of transmitting the medicament through the skin to a portion of the skin of the animal.

The invention will now be further described, though only by way of illustration, with reference to the accompanying drawings, in which:

FIG. 1 is a cross-sectional view through an ear of an animal having two devices of the present invention attached thereto;

FIG. 2 is a plan view of the ear and one attached device of FIG. 1;

FIG. 3 is a cross-sectional view through an ear of an animal having a second device of the present invention attached thereto;

FIG. 4 is a plan view of the ear and the attached device of FIG. 3;

FIG. 5 is a top plan view of a device for attachment to the tail of an animal;

FIG. 6 is a cross-sectional view of the line VI — VI of FIG. 5; and

FIG. 7 is a perspective view of the device of FIGS. 5 and 6 in position on the tail of an animal.

In FIGS. 1 and 2, an ear 1 of an animal has attached thereto by means of fastening pin 2 two circular aluminium domed members 3 and 4, each of which has an annular basal surface area 5 and 6 respectively in contact with the ear, and a depression 7 and 8 respectively, Between the depressions 7 and 8 and the ear 1 is contained a medicament 9 in the form of a cream. It will be readily appreciated, however, that the medicament 9 could alternatively be in the form of a solution absorbed onto a porous, solid carrier, for example cotton wool.

The device shown in FIGS. 3 and 4 comprises a domed nylon member 10 having an annular basal surface area 11 in contact with the ear 12 of an animal. Within a circular depression 13 in the domed member 10 is located a solid disc 14 of a medicament composition capable of passing the medicament through the skin of the animal. In a deeper elongate depression 15 in the domed member 10 is located a leaf spring 16 which bears upon a metal support disc 17 for the medicament composition 14 and urges the composition 14 against the ear 12. Through the basal surface area 11 and through the ear 12 are provided four pins 18 which secure the device to the ear.

The device shown in FIGS. 5 to 7 is constructed of a plastics material and is of elongate shape having a basal surface area 19 adapted to contact the skin of the tail of a cow. There is also provided an elongate rectangular depression 20 which contains a medicament solution capable of passing the medicament through the skin, absorbed onto a cotton wool pad 21. At one end of the device there are provided two flexible plastics strips 22 and 23 which are pierced with holes 24 adapted to coact by press fit with projections 25 provided at the other end of the device to secure the device circumferentially around the tail 26 as shown in FIG. 7. In FIG. 6 the device is shown before use, having a strippable foil sheet 27 heat sealed around the basal surface area 19 to retain the medicament in a sterile condition during storage within the depression 20. This is naturally removed before application of the device to the tail of the animal.

The invention will now be further described, though only by way of illustration, in the following Examples.

EXAMPLE 1

A device as described above with reference to FIGS. 5 to 7 containing a pad of cotton wool (10g) onto which was absorbed 50 mls of a solution of laevo-2,3,5,6-tetrahydro-6-phenylimidazo [2,1-b]thiazole (12g) in a mixture of Aromasol H (a proprietary hydrocarbon mixture) (70parts), methyl ethyl ketone (10 parts) and mineral oil (20 parts) was strapped onto the base of the tail of a 200 kg calf infected 4 weeks previously with *Cooperia oncophora* and which was passing worm eggs in the faeces. Within 2 days of applying the device eggs were not detectable in the foeces. The calf was challenged with a new infection of *Cooperia oncophora* at weekly intervals after applying the device. No worm eggs appeared in the faeces for 6 weeks following application of the device.

EXAMPLE 2

A device as described above with reference to FIGS. 3 and 4 containing a composition, in the form of a solid disc, of laevo-2,3,5,6-tetrahydro-6-phenylimidazo[2,1-b]thiazole (3g), polyethylene glycol (carbowax 4000) (3g) and isopropyl alcohol (1g) was pinned to the ear of a 50 kg worm free sheep. On the day of application and thereafter at weekly intervals the sheep was infected with larvae of *Haemonchus contortus*. No eggs appeared in the sheep faeces until 7 weeks after applying the device.

EXAMPLE 3

A device comprising a plastic material cup attached to an elastic harness was applied to the body of sheep weighing from 28 kg to 30 kg so that the mouth of the cup was maintained firmly in contact with the animal's skin. The cup was packed with absorbent cotton wool having absorbed thereon a 10% solution of the laevo isomer of 2,3,5,6-tetrahydro-6-phenyl-imidazo]2,1-b]thiazole in a mixture of 20% dimethyl sulphoxide and 80% Aromasol H (a proprietary hydrocarbon mixture). The animals were challenged with infective larvae of *haemonchus contortus* on the day the device was applied, and weekly thereafter. It was not found possible to establish the nematode infection within 3 weeks of applying the device.

EXAMPLE 4

The device described above in Example 3 but containing cotton wool impregnated with 40 mls of a 10% solution of 4,5,6-trichloro-7-(ethylsulphamoyl)-2(trifluoroemthyl)-benzimidazole in a mixture of 20% dimethyl sulphoxide and 80% Aromasol H (a proprietary hydrocarbon mixture). 24 hours after application of the device to an 18 kg sheep, an existing infection of *Haemonchus contortus* was eliminated and the animal could not be further infected for a period of 3 weeks. The treatment also eliminated an existing infection of *Lucilia sericata* and prevented reinfection for a further 3 weeks.

We claim:
1. A method of administering a systemically active anthelmintic compound over an extended period to an animal through its skin, which method comprises contacting the skin of the animal with a composition containing the anthelmintic compound and a carrier capable of transmitting the compound through the skin, said composition being contained within one or more depressions provided in the basal surface area of a device having means by which it is attached to the animal such that the basal surface area thereof contacts the skin of the animal.

2. A method according to claim 1, wherein the rate of transmission of the anthelmintic compound through the skin is propylactic but non-curative.

3. A method according to claim 1, wherein the anthelmintic compound is selected from the group consisting of:
2,3,5,6-tetrahydro-6-phenylimidazo(2,1-b)thiazole) or a salt thereof,
2-(4-thiazoly)benzimidazole,
carbon tetrachloride,
methyl-5-butyl-benzimidazole-2-carbamate
2,2'-methylenebis-(3,4,6-trichlorophenol) or a salt thereof,
2-(2-methoxyethyl)pyridine or a salt thereof,
4-hydroxy-3-iodo-5-nitrobenzonitrile or a salt thereof,
3'-chloro-4'-(p-chlorophenoxy)-3,5-diiodosalicylanilide or a salt thereof,
3,3',5,5',6-pentachloro-2,2'-dihydroxybenzanilide or a salt thereof,
methyl 1-butylcarbomoyl)benzimidazole-2-carbamate,
methyl benzimidazole-2-carbamate,
diethyl 4,4'-o-phenylenebis(3-thioallophanate,
methyl 5-propoxybenzimidazole-2-carbamate,
triphenylbismuth triphenylbismuth dinitrate,
triphenylbismuth dichloride,
triphenylbismuth difluoride,
4,5,6-trichloro-7-(diethylsulphamoyl)-2-(trifluoromethyl)benzimidazole,
4-bromo-5,6-dichloro-7-(diethylsulphamoyl)-2-(trifluoromethyl)benzimidazole,
4,5,6-tribromo-7-(diethylsulphamoyl-2-(trifluoromethyl)benzimidazole,
4,6-dibromo-5-chloro-7-(diethylsulphamoyl)-2-(trifluoromethyl)benzimidazole,
4,5,6-trichloro-7-(ethylsulphamoyl)-2-(trifluoromethyl)benzimidazole;
4,5,6-trichloro-7-(methylsulphamoyl)-2-(trifluoromethyl)benzimidazole,
4,5,6-trichloro-7-(n-propylsulphamoyl)-2-(trifluoromethyl)benzimidazole,
and salts of said benzimidazoles.

4. A method according to claim 3, wherein the anthelmintic compound is laevo-2,3,5,6-tetrahydro-6-phenylimidazo(2,1-b)thiazole.

* * * * *